United States Patent
Sakaue et al.

(10) Patent No.: US 7,371,550 B2
(45) Date of Patent: May 13, 2008

(54) CHOLESTEROL OXIDASE STABLE IN THE PRESENCE OF SURFACTANT

(75) Inventors: Ryoichi Sakaue, Chiba (JP); Naoki Kajiyama, Chiba (JP)

(73) Assignee: Kikkoman Corporation, Chiba (JP)

(*) Notice: Subject to any disclaimer, the term of this patent is extended or adjusted under 35 U.S.C. 154(b) by 0 days.

(21) Appl. No.: 11/448,048

(22) Filed: Jun. 7, 2006

(65) Prior Publication Data

US 2007/0010000 A1    Jan. 11, 2007

(30) Foreign Application Priority Data

Jun. 8, 2005    (JP) .................. P. 2005-167779

(51) Int. Cl.
  *C12N 9/02*    (2006.01)
  *C07H 21/04*   (2006.01)
  *C12P 21/06*   (2006.01)

(52) U.S. Cl. .................. 435/189; 435/69.1; 435/325; 435/320.1; 536/23.2

(58) Field of Classification Search ............... 435/189, 435/252.1

See application file for complete search history.

(56) References Cited

U.S. PATENT DOCUMENTS

2003/0153051 A1*   8/2003   Aono et al. ............... 435/70.1

FOREIGN PATENT DOCUMENTS

JP    2002 2065271    3/2002

OTHER PUBLICATIONS

Doukyo et al., Accession No. ABB09141, Jun. 27, 2002.*
Whisstock, et al. Quarterly Rev. Biophy. 2003, 36, pp. 307-340.*
N. Doukyu et al.; Applied Microbiology and Biotechnology, 2001, vol. 57, No. 1-2, pp. 146-152.
English language Abstract of JP 2002-065271.

* cited by examiner

*Primary Examiner*—Rebecca E. Prouty
*Assistant Examiner*—Younus Meah
(74) *Attorney, Agent, or Firm*—Greenblum & Bernstein, P.L.C.

(57) ABSTRACT

A novel cholesterol oxidase having stability in the presence of surfactant and a gene encoding the novel cholesterol oxidase.

1 Claim, 2 Drawing Sheets

△ : 0.1M ACETATE BUFFER
○ : 0.1M PHOSPHATE BUFFER
● : 0.1M Tris-HCl BUFFER
□ : 0.1M NaHCO3-NaOH BUFFER BUFFER: 0.1M PHOSPHATE BUFFER, pH 7.0

CHOLESTEROL OXIDASE STABLE IN THE PRESENCE OF SURFACTANT

BACKGROUND OF THE INVENTION

1. Field of the Invention

The present invention relates to a novel cholesterol oxidase having stability in the presence of surfactant and a gene encoding the novel cholesterol oxidase.

2. Brief Description of the Background Art

A cholesterol oxidase is an oxidase which catalyses the reaction between 3β-hydroxysteroid and oxygen to thereby form the corresponding 3-oxosteroid and hydrogen peroxide. Its research and development have so far been made for the purpose of applying it to the measurement of cholesterol concentration in body fluids (e.g., JP-A-6-169765), production of cholesterol derivatives (e.g., JP-A-6-113883), insecticides (e.g., U.S. Pat. No. 5,558,862), detergents (e.g., WO 89/09813) and the like.

It is known that the enzyme is produced by many genera of microorganisms such as *Streptomyces* (e.g., JP-A-62-285789 (corresponding to EP-A-0560983)), *Brevibacterium* (e.g., JP-A4-218367 (corresponding to EP-A-0452112)), *Rhodococcus* (e.g., JP-T-3-503487 (corresponding to WO 90/05788)) and *Pseudomonas* (e.g., JP-A-6-189754).

The cholesterol oxidase isolated from *Burkholderia cepacia* ST-200 (*Pseudonmnas* sp. ST-200 according to the old classification, has been deposited on Feb. 4, 1998 in National Institute of Bioscience and Human Technology (NIBH), Ministry of International Trade and Industry, (1-3, Higashi 1-chome, Tsukuba-shi, Ibarki, Japan), its deposit number is FERM MP-6661) (e.g., Japanese Patent No. 3,241,712 (corresponding to US-A-2003/153051)) is characterized in that its product when cholesterol is used as the substrate is different, its reaction mechanism is different and it has high organic solvent resistance and temperature stability, in comparison with other cholesterol oxidase so far known. Since a gene of the cholesterol oxidase derived from *Burkholderia cepacia* ST-200 has been cloned, high level production of a recombinant cholesterol oxidase can be carried out in various hosts through its secretion or intracellular accumulation (e.g., JP-A-2002-65271).

The characteristics required for an enzyme to be used in an agent for clinical diagnosis are, in most cases, high reactivity and specificity to the object and thermal stability which shows influence upon preservation stability of the product, but in the case of the measurement of cholesterol, a surfactant is frequently prescribed at a high concentration for the purpose of measuring the object at a high specificity, so that in addition to the above-described characteristics, a preservation stability in the coexistence of a surfactant is also strongly in demand for the enzyme to be used. Although the cholesterol oxidase derived from *Burkholderia cepacia* ST-200 has the above-described excellent properties, this enzyme is inferior in terms of the preservation stability in the coexistence of a surfactant, and therefore it is difficult to apply the enzyme to a cholesterol measuring reagent.

Regarding the surfactant to be used in the cholesterol measuring system, 1-pentanesulfonate, 1-hexanesulfonate, 1-heptanesulfonate, 1-octanesulfonate, polyoxyethylene alkyl ether sulfate, sodium dodecylbenzenesulfonate, a cholic acid salt (sodium cholate), cholic acid, dehydrocholate, deoxycholic acid, sodium deoxycholate, sodium taurodeoxycholate, N,N-bis(3-D-gluconamidopropyl)cholamide, N,N-bis-3-D-gluconamidopropylcholamide, dodecylbenzenesulfonate, lauroylsarcosine and the like are used as anionic surfactants (e.g., JP-A-8-116996, Japanese Patent No. 2,799, 835 (corresponding to JP-A-7-13607), JP-A-11-56395, JP-A-2000-60600 (corresponding to EP-A-0964249), JP-A-2002-142799 (corresponding to EP-A-1342792), Japanese Patent No. 3,529,081 (corresponding to JP-A-10-232219), JP-A-10-84997 (corresponding to EP-A-0821239)). In addition, n-dodecyltrimethylammonium chloride, hexadecylpyridinium chloride and the like are used as cationic surfactants (e.g., JP-A-10-84997 (corresponding to EP-A-0821239)).

As nonionic surfactants, polyoxyethylene alkyl ether, polyoxyethylene alkyl phenyl ether, polyoxyethylene-polyoxypropylene condensate, acyl polyoxyethylene sorbitan ester, alkyl polyoxyethylene ether, n-dodecyl-β-D-maltoside, sucrose monolaurate, polyoxyethylene lauryl ether, polyoxyethylene alkylene phenyl ether, polyoxyethylene alkylene tribenzyl phenyl ether, polyoxyethylene glycol p-t-octyl phenyl ether, polyoxyethylene higher alcohol ether, polyoxyethylene fatty acid ester, polyoxyethylene sorbitan fatty acid ester, sorbitan fatty acid ester, polyoxyethylene sorbitol fatty acid ester, polyoxyethylene alkylamine, glycerol fatty acid ester, n-octyl-β-D-thioglucoside, cetyl ether (C16), lauryl ether (C12), oleyl ether, behenyl ether (C20), polyoxyethylene monolaurate and the like are used (e.g., Japanese Patent No. 2,799,835 (corresponding to JP-A-7-13607), JP-A-11-56395, JP-A-2000-60600 (corresponding to EP-A-0964249), JP-A-2002-142799 (corresponding to EP-A-1342792), Japanese Patent No. 3,529,081 (corresponding to JP-A-10-232219), JP-A-10-84997 (corresponding to, EP-A-0821239), JP-A-2000-325097, JP-A-2001-124780, JP-A-2000-116400, JP-A-9-299, JP-A-2001-346598, JP-A-9-224697, Japanese Patent No. 3,193,634 (corresponding to JP-A-9-313200), JP-A-10-210999).

In addition, betaine derivatives, alkylbetaine derivatives, imidazoliumbetaine derivatives, sulfobetaine derivatives, aminocarboxylic acid derivatives, imidazoline derivatives, amine oxanoide derivatives, bile acid derivatives and the like are used as ampholytic surfactants (e.g., JP-A-2000-60600 (corresponding to EP-A-0964249), JP-A-10-84997 (corresponding to EP-A-0821239), JP-A-2000-325097, JP-A-2001-124780).

SUMMARY OF THE INVENTION

An object of the present invention is to provide a cholesterol oxidase having high stability in the presence of surfactant and a gene encoding the same, by overcoming disadvantages of by the conventional cholesterol oxidase derived from the *Burkholderia cepacia* ST-200.

This and other objects of the present invention have been accomplished by a novel cholesterol oxidase having stability in the presence of surfactant and a gene encoding the novel cholesterol oxidase.

DETAILED DESCRIPTION OF THE INVENTION

Figure 1:
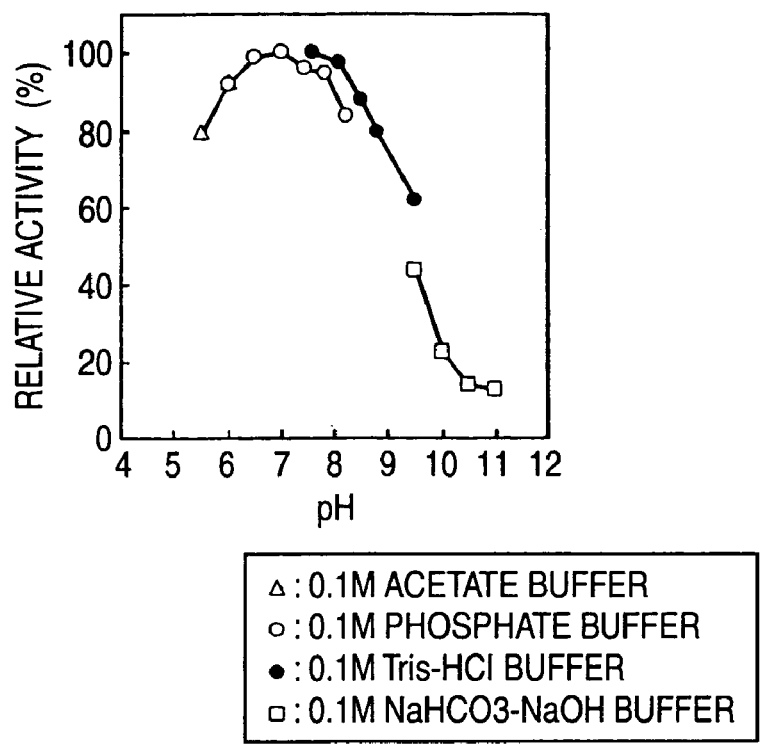
FIG. 1 is a graph showing an optimum pH of the oxidase of the present invention.

The present inventors have conducted intensive studies in order to solve the above-described problems and found, as a result of modification of the cholesterol oxidase gene derived from *Burkholderia cepacia* ST-200 (described in JP-A-2002-65271), that a novel cholesterol oxidase having high stability in the presence of a surfactant can be obtained, and thus the present invention has been accomplished.

That is, the present invention relates to the following (1) to (3):

(1) A novel cholesterol oxidase having the following physicochemical properties, wherein the cholesterol oxidase has improved stability to a surfactant:
(a) action and substrate specificity: it acts on cholesterol to convert it into cholest-5-en-3-one; it acts on cholest-5-en-3-one and converts it into 6β-perhydroxycholest-4-en-3-one; it acts on 3β-sterol but does not act on 3α-hydroxysteroid, and
(b) molecular weight: about 60,000 (SDS-PAGE).
(2) A protein having cholesterol oxidase activity, which is a protein selected from the group consisting of the following (a) to (f):
(a) a protein comprising the amino acid sequence represented by SEQ ID NO:2,
(b) a protein consisting of an amino acid sequence in which at least one amino acid is deleted, substituted, added and/or inserted in the amino acid sequence represented by SEQ ID NO:2, and having cholesterol oxidase activity,
(c) a protein consisting of an amino acid sequence which has 80% or more homology to the amino acid sequence represented by SEQ ID NO:2, and having cholesterol oxidase activity,
(d) a protein comprising the amino acid sequence represented by SEQ ID NO:5,
(e) a protein consisting of an amino acid sequence in which at least one amino acid is deleted, substituted, added and/or inserted in the amino acid sequence represented by SEQ ID NO:5, and having cholesterol oxidase activity, and
(f) a protein consisting of an amino acid sequence which has 80% or more homology with the amino acid sequence represented by SEQ ID NO:5, and having cholesterol oxidase activity.
(3) A gene which is a DNA selected from the group consisting of the following (a) to (f):
(a) a DNA comprising the nucleotide sequence represented by SEQ ID NO:4,
(b) a DNA which hybridizes with a full length of a DNA consisting of the nucleotide sequence represented by SEQ ID NO:4, with continued 15 or more bases in a DNA consisting of the nucleotide sequence represented by SEQ ID NO:4, or with a DNA consisting of a nucleotide sequence complementary thereto, under stringent conditions, and which encodes a protein having cholesterol oxidase activity,
(c) a DNA which has 80% or more homology with a full length of a DNA consisting of the nucleotide sequence represented by SEQ ID NO:4 or with continued 15 or more bases in the nucleotide sequence represented by SEQ ID NO:4, and which encodes a protein having cholesterol oxidase activity,
(d) a DNA comprising the nucleotide sequence represented by SEQ ID NO:6,
(e) a DNA which hybridizes with a full length of a DNA consisting of the nucleotide sequence represented by SEQ ID NO:6, with continued 15 or more bases in a DNA consisting of the nucleotide sequence represented by SEQ ID NO:6, or with a DNA consisting of a nucleotide sequence complementary thereto, under stringent conditions, and which encodes a protein having cholesterol oxidase activity, and
(f) a DNA which has 80% or more homology with a full length of a DNA consisting of the nucleotide sequence represented by SEQ ID NO:6 or with continued 15 or more bases in a DNA consisting of the nucleotide sequence represented by SEQ ID NO:6, and which encodes a protein having cholesterol oxidase activity.

In the present invention, a cholesterol oxidase having further higher stability to surfactants, which is industrially useful in applying it to a reagent as an enzyme for clinical diagnosis, and a gene encoding the same are provided.

The novel cholesterol oxidase of the present invention (hereinafter referred to as "oxidase of the present invention") is a cholesterol oxidase having the following physicochemical properties, wherein its preservation stability in the presence of surfactants is improved:
(a) action and substrate specificity: it acts on cholesterol to convert it into cholest-5-en-3-one; it acts on cholest-5-en-3-one and converts it into 6β-perhydroxycholest-4-en-3-one; it acts on 3β-sterols but does not act on 3α-hydroxysteroid, and
(b) molecular weight: about 60,000 (SDS-PAGE).

The molecular weight is obtained in the usual way by the SDS-PAGE method using Multigel 10/20 (manufactured by Daiichi Pure Chemicals).

Thus, the oxidase of the present invention is different from any one of the conventional cholesterol oxidases in terms of its physicochemical properties and therefore is a novel cholesterol oxidase. Accordingly, the oxidase of the present invention can be used in a kit reagent as an enzyme for clinical diagnosis use having superior preservation stability.

As the oxidase of the present invention, oxidases derived from various organisms obtained by screening from the natural world and oxidases obtained by modifying conventionally known cholesterol oxidases can be exemplified, and the following oxidase of the present invention (c), (d), (e), (f), (g) or (h) can, for example, be cited:
(c) a cholesterol oxidase comprising the amino acid sequence represented by SEQ ID NO:2;
(d) a cholesterol oxidase consisting of an amino acid sequence in which at least one amino acid is deleted, substituted, added and/or inserted in the amino acid sequence represented by SEQ ID NO:2;
(e) a cholesterol oxidase consisting of an amino acid sequence having 80% or more homology with the amino acid sequence represented by SEQ ID NO:2;
(f) a cholesterol oxidase comprising the amino acid sequence represented by SEQ ID NO:5;
(g) a cholesterol oxidase consisting of the amino acid sequence in which at least one amino acid is deleted, substituted, added and/or inserted in the amino acid sequence represented by SEQ ID NO:5;
(h) a cholesterol oxidase consisting of an amino acid sequence which has 80% or more homology with the amino acid sequence represented by SEQ ID NO:5.

In this connection, the term "at least one amino acid is deleted, substituted, added and/or inserted" means that from one to several amino acid(s) is/are deleted, substituted, added and/or inserted, for example, from 1 to 20, preferably from 1 to 10, and more preferably from 1 to 5 amino acid(s) is/are deleted, substituted, added and/or inserted. In addition, the term "has 80% or more homology" is not particularly limited, so long as its homology with the amino acid sequence represented by SEQ ID NO:2 or 5 is 80% or more, and the homology is, for example, 80% or more, preferably 90% or more, and most preferably 95% or more.

As the cholesterol oxidase gene encoding the novel cholesterol oxidase of the present invention (hereinafter referred to as "gene of the present invention"), a gene encoding the above-described oxidase of the present invention (c), (d), (e), (f), (g) or (h) and also a gene encoding the oxidase of the present invention comprising the following DNA (a), (b), (c), (d), (e) or (f) can, for example, be cited:

(a) a DNA comprising the nucleotide sequence represented by SEQ ID NO:4;
(b) a DNA consisting of a nucleotide sequence which hybridizes with a full length of the nucleotide sequence represented by SEQ ID NO:4, with continued 15 or more bases in the nucleotide sequence represented by SEQ ID NO:4, or with a nucleotide sequence complementary thereto, under stringent conditions;
(c) a DNA consisting of a nucleotide sequence which has 80% or more homology with a full length of the nucleotide sequence represented by SEQ ID NO:4 or with continued 15 or more bases in the nucleotide sequence represented by SEQ ID NO:4;
(d) a DNA comprising the nucleotide sequence represented by SEQ ID NO:6.
(e) a DNA consisting of a nucleotide sequence which hybridizes with a full length of the nucleotide sequence represented by SEQ ID NO:6, with continued 15 or more bases in the nucleotide sequence represented by SEQ ID NO:6, or with a nucleotide sequence complementary thereto, under stringent conditions;
(f) a DNA consisting of a nucleotide sequence which has 80% or more homology with a full length of the nucleotide sequence represented by SEQ ID NO:6 or with continued 15 or more bases in the nucleotide sequence represented by SEQ ID NO:6.

In this connection, the term "DNA which hybridizes under stringent conditions" means a DNA obtained by employing colony hybridization, plaque hybridization, Southern blot hybridization or the like using the DNA as the probe, and a DNA which can be identified by carrying out hybridization at 65° C. using a filter on which DNA samples derived from colonies or plaques or fragments of the DNA samples are fixed, and then washing the filter at 65° C., can be specifically exemplified. The hybridization can be carried out in accordance with the method described in *Current Protocols in Molecular Biology* (WILEY Interscience, 1989) or the like. As the DNA which hybridizes under stringent conditions, a DNA having a certain level of homology with the nucleotide sequence of DNA to be used as the probe can be exemplified. The homology of the "DNA consisting of a nucleotide sequence which has 80% or more homology with a full length of the nucleotide sequence or with continued 15 or more bases in the nucleotide sequence" according to the present invention is, for example, 80% or more, preferably 90% or more, and most preferably 95% or more.

Next, the methods for obtaining the oxidase of the present invention and the gene of the present invention are described.

The oxidase of the present invention can be obtained from the natural world by screening the enzyme derived from a microorganism, an animal or a plant. In addition, the oxidase of the present invention can also be obtained by modifying a cholesterol oxidase which has a different physicochemical property from that of the enzyme of the present invention (hereinafter referred to as "oxidase having different property") using genetic engineering technique, mutation treatment or the like. As the oxidase having different property according to the present invention, the conventionally known oxidases and the like described above can be exemplified, but it may also be a cholesterol oxidase newly obtained by carrying out screening or a cholesterol oxidase obtained by carrying out modification through genetic engineering technique. For example, the cholesterol oxidase derived from *Burkholderia cepacia* ST-200 (described in Japanese Patent No. 3,241,712 (corresponding to US-A-2003/153051) and JP-A-2002-65271) and the like can be cited as the conventionally known oxidases. The above-described cholesterol oxidase is originally a secretory protein which has a signal sequence, but this may be used by keeping back the signal sequence or may be produced in the cells by removing the signal sequence.

Examples of the method for modifying a physicochemical property of the oxidase having different property include a method in which a microorganism capable of producing modified oxidase of the present invention is obtained, for example, by applying ultraviolet rays, X-rays or a radiation to the microorganism capable of producing the oxidase, or by allowing a mutagen, such as ethyl methanesulfonate, N-methyl-N'-nitro-N-nitrosoguanidine or nitrous acid, to contact with the microorganism, and then the oxidase of the present invention is obtained from the thus obtained microorganism.

However, in general, the oxidase of the present invention can be obtained by modifying a gene encoding an oxidase having a different property using genetic engineering technique. As the gene encoding an oxidase having a different property to be used in the present invention, any gone encoding a cholesterol oxidase can be used, with the proviso that it is a gene from which the oxidase of the present invention can be obtained by its modification.

In order to obtain a gene encoding an oxidase having a different property to be used in the present invention, a generally used gene cloning method is used. For example, chromosomal DNA or mRNA is extracted from microbial cells or various other cells capable of producing an oxidase having a different property, by a usual method such as the method described in *Current Protocols in Molecular Biology* (WILEY Interscience, 1989). In addition, cDNA can be synthesized using mRNA as the template. A library of the thus obtained chromosomal DNA or cDNA is prepared. Subsequently, a full length DNA comprising the gene of interest can be obtained by a method in which an appropriate probe DNA is synthesized based on the amino acid sequence of the above-described oxidase having a different property, and the gene of interest is screened from the chromosomal DNA or cDNA library using this probe, or by a method in which appropriate DNA primers are prepared based on the above-described amino acid sequence, DNA fragments comprising the gene fragments of interest are amplified using these primers by carrying out an appropriate polymerase chain reaction (PCR), such as 5' RACE, 3' RACE, and then these fragments are ligated. As a preferred example of the gene encoding an oxidase having a different property, obtained in this manner, the cholesterol oxidase gene derived from *Burkholderia cepacia* ST-200 (described in JP-A-2002-65271) and the like can be cited, It is desirable from the viewpoint of handling that these genes are connected to various vectors in the usual way, and they can be obtained for example by extracting and purifying them from a recombinant plasmid pCox4 DNA (described in JP-A-

2002-65271) which comprises the gene encoding an oxidase having a different property derived from the isolated *Burkholderia cepacia* ST-200, using, for example, QIAGEN (manufactured by Qiagen). In this connection, the vector DNA which can be used in the present invention is not limited to the above-described plasmid vector DNA, and other plasmid vector DNA, such as a plasmid vector DNA, a bacteriophage vector DNA and the like can also be used. Specifically, for example, pBluescript II SK+ (manufactured by STRATAGENE) and the like are desirable.

Next, the oxidase of the present invention can be obtained by modifying the gene obtained by the above-described method encoding an oxidase having a different property. That is, according to the present invention, by the modification of the gene encoding an oxidase having a different property, the amino acid sequence of the oxidase having a different property, translated by the gene, is modified. As a result, various cholesterol oxidases having a different property, including the oxidase of the present invention, which are different from the oxidase of before the modification having a different property, are obtained.

The gene to be used in the modification, encoding an oxidase having a different property, is not particularly limited, but the gene derived from *Burkholderia cepacia* ST-200 encoding an oxidase having a different property (JP-A-2002-65271, SEQ ID NO:3) and the like can be exemplified as an embodiment of the present invention. In addition, those in which the nucleotide sequence is modified in such a manner that amino acid residues are not added, deleted, substituted and/or inserted, or added, deleted, substituted and/or inserted, in order to express this gene in a host organism, can also be exemplified.

As the method for modifying the above-described gene, any conventionally known method can be used, and examples include a method in which as chemical mutagen such as hydroxylamine or nitrous is allowed to contact with the above-described recombinant plasmid pCox4 DNA (described in JP-A-2002-65271), a point mutation method such as random conversion using PCR method, a site-directed mutagenesis which is a conventionally known method for generating a site-directed substitution or deletion mutation using a commercially available kit, and a method in which this recombinant plasmid DNA is selectively cleaved, a selected oligonucleotide is removed therefrom or added thereto, and then its ligation is carried out, namely an oligonucleotide mutagenesis. Subsequently, the recombinant DNA after the above-described treatment is purified using a desalting column, QIAGEN (manufactured by Qiagen) or the like to obtain various recombinant DNA samples. In that case, it may be effective to use a recombinant DNA prepared by removing a nucleotide sequence encoding the amino terminus side signal sequence of the cholesterol oxidase, from the pCox4 DNA, and ATG encoding the initiation methionine is added thereto instead, or a recombinant DNA prepared by substituting the amino terminus side-encoded nucleotide sequence for a sequence suited for expressing it in a host organism such as *Escherichia coli*.

For example, by carrying out transformation or transduction of *Escherichia coli* K12, preferably *Escherichia coil* JM109 or DH5α (both manufactured by TOYOBO), XL-Blue (manufactured by Funakoshi) or the like using various recombinant DNAs obtained in this manner, transformants or transduction products containing various species of recombinant DNA having modified cholesterol oxidase gene fragments can be obtained. Thereafter, in the case of transformants, for example, the intended transformant of the present invention having stability in the presence of a surfactant (oxidase producer strain of the present invention) is selected from the obtained transformants (contain therein recombinant plasmid DNA molecules which comprise various species of mutated cholesterol oxidase gene).

Next, in order to select the oxidase producer strain of the present invention, the following method can for example be employed. Firstly, colonies of the obtained above-described transformants are put into sterilized LB liquid medium and sub-cultured in a ampicillin-added sterilized 96-well plate. When they are sufficiently grown, a lytic agent such as lysozyme is added thereto and allowed to stand at 37° C. for about 1 hour for cell lysis. When the cells are lysed, 0.1 M MES buffer (pH 7.0) containing an appropriate surfactant and 0.2% bovine serum albumin is dispensed at 50 μl into wells of a 96-well plate, and the lysed culture liquids are added to respective wells at 50 μl and treated at 37° C. for 5 hours. Thereafter, 0.1 M potassium phosphate buffer (pH 7.0) containing cholesterol as the substrate, Triton X-100, sodium cholate, peroxidase, phenol and 4-aminoantipyrine is added and suspended at 100 μl, and the degree of reddish purple color development is observed. The coloring test is also cared out by the same process on the oxidase producer strains of before the modification having a different property, and the transformant of interest is selected by comparing the results.

The surfactant to be used may be any surfactant which is used in the above-described cholesterol measuring system, but preferred anionic surfactants include 1-pentanesulfonate, 1-hexanesulfonate, 1-heptanesulfonate, 1-octanesulfonate, polyoxyethylene alkyl ether sulfate (trade name: Emal 20C, Emal NC-35 (both manufactured by KAO), sodium dodecylbenzeresulfonate, a cholic acid salt (sodium cholate), cholic acid, dehydrocholate, deoxycholic acid, sodium deoxycholate, sodium taurodeoxycholate, N,N-bis (3-D-gluconamidopropyl)cholamide, N,N-bis-3-D-gluconamidopropylcholamide, dodecylbenzenesulfonate, lauroylsarcosine and the like. Preferred cationic surfactants include n-dodecyltrimethylammonium chloride, hexadecylpyridinium chloride and the like. Preferred nonionic surfactants include polyoxyethylene alkyl ether (trade name: Emalgen 220, Emalgen 104P, Emalgen 108, Emalgen 408, etc. (manufactured by KAO)), polyoxyethylene alkyl phenyl ether (trade name: Emalgen 903, Emalgen 909, Emalgen 913, etc. (manufactured by KAO)), polyoxyethylene-polyoxypropylene condensate (trade name: Pluronic F88 (manufactured by Asahi Denka), acyl polyoxyethylene sorbitan ester (trade name: Tween 21, Tween 81, Tween 20, Tween 40, Tween 60, Tween 80, Tween 85, Emasol 4130, etc.), alkyl polyoxyethylene ether (trade name: Atlas G2127, Brij 36T, Briji 56, etc.), n-dodecyl-β-D-maltoside, sucrose monolaurate, polyoxyethylene lauryl ether (trade name: Emalgen 120, etc.), polyoxyethylene alkylene phenyl ether (trade name: Emalgen A60, etc.), polyoxyethylene alkylene tribenzyl phenyl ether (trade name: Emalgen B66, etc.), polyoxyethylene glycol p-t-octyl phenyl ether (trade name: Triton X100), polyoxyethylene higher alcohol ether (trade name: Emalgen 705, Emalgen 709, etc.), polyoxyethylene fatty acid ester, polyoxyethylene sorbitan fatty acid ester, sorbitan fatty acid ester, polyoxyethylene sorbitol fatty acid ester, polyoxyethylene alkylamine, glycerol fatty acid ester, n-octyl-β-D-glucoside, polyoxyethylene glycol monododecyl ether, n-octyl-β-D-thioglucoside, cetyl ether (C16), lauryl ether (C12), oleyl ether, behenyl ether (C20), polyoxyethylene monolaurate and the like. Preferred ampholytic surfactants include betaine derivatives, alkylbetaine derivatives, imidazoliumbetaine derivatives, sulfobetaine derivatives, aminocarboxylic acid derivatives, imidazoline derivatives, amine oxanoide derivatives, bile acid derivatives and the like. Among these, nonionic surfactants are more preferable.

In this manner, a transformant having the ability to produce the oxidase of the present invention can be obtained. Examples include the oxidase of the present invention comprising the amino acid sequence represented by SEQ ID NO:2, obtained by subjecting the *Burkholderia cepacia* ST-200-derived cholesterol oxidase having the amino acid sequence represented by SEQ D NO:1 to the above-described modification method, and the like. Furthermore, if necessary, a modified oxidase of the present invention having further increased stability to a surfactant and a transformant having the ability to produce the same can also be obtained by further repeating modification of the gene of the present invention by the above-described modification method using this transformant having the ability to produce the oxidase of the present invention. That is, according to the present invention, a cholesterol oxidase consisting of an amino acid sequence in which at least one amino acid is deleted, substituted, added and/or inserted in the amino acid sequence represented by SEQ ID NO:2 or 5, a cholesterol oxidase consisting of an amino acid sequence which has 80% or more homology with the amino acid sequence represented by SEQ ID NO:2 or 5 and the like are also included in the oxidase of the present invention. For example, an oxidase of the present invention (R7) which is shown later in Examples and the like can be specifically exemplified. In the R7, 3 amino acid residues are substituted in the amino acid sequence represented by SEQ ID NO:2, and it has a homology of 90% or more. In addition, as an example of the thus obtained transformant capable of producing the oxidase of the present invention, *Escherichia coli* (*E. coli*) JM109 (pNCP1) which produces an oxidase of the present invention (R1) consisting of the amino acid sequence represented by SEQ ID NO:2 and having 80% of residual activity ratio in the coexistence of a surfactant can be cited.

Also, a gene (SEQ ID NO:6) of the above-described oxidase of the present invention (R1) can be cited as an example of the gene of the present invention. The plasmid pNCP1 containing the gene which comprises SEQ ID NO:6 encoding SEQ ID NO:5 has been deposited on May 27, 2005 in International Patent Organism Depositary, National Institute of Advanced Industrial Science and Technology, as FERM BP-10343. In addition, genes encoding the cholesterol oxidase of the present invention such as a cholesterol oxidase consisting of an amino acid sequence in which at least one amino acid is deleted, substituted, added and/or inserted in the amino acid sequence represented by SEQ ID NO:2 or 5 and a cholesterol oxidase consisting of an amino acid sequence which has 80% or more homology with the amino acid sequence represented by SEQ ID NO:2 or 5, and genes encoding the cholesterol oxidase of the present invention such as a DNA consisting of a nucleotide sequence which hybridizes with a full length of the nucleotide sequence represented by SEQ ID NO:4 or 6, with continued 15 or more bases in the nucleotide sequence represented by SEQ ID NO:4 or 6, or with a DNA consisting of a nucleotide sequence complementary thereto, under stringent conditions, and a DNA consisting of a nucleotide sequence which has 80% or more homology with a full length of the nucleotide sequence represented by SEQ ID NO:4 or 6 or with continued 15 or more bases in the nucleotide sequence represented by SEQ ID NO:4 or 6, can be exemplified as the gene of the present invention Specific examples of the "continued 15 or more bases" include a nucleotide sequence of from 4 to 186 bases as a partial sequence of SEQ ID NO:6 and the like. In addition, a sequence in which a nucleotide sequence of from 130 to 312 bases of SEQ ID NO:4 was exchanged with the nucleotide sequence of from 4 to 186 bases of SEQ ID NO:6 also encodes the amino acid sequence of SEQ ID NO:2, so that this can also be cited as an example of the DNA consisting of a nucleotide sequence which has 80% or more homology.

Next, the oxidase of the present invention is produced by culturing a microorganism capable of producing the oxidase of the present invention using a medium and collecting the cholesterol oxidase from the culture mixture. Any microorganism can be used in the production of the oxidase of the present invention, with the proviso that it is a microorganism which has the ability to produce the oxidase of the present invention. Examples include the transformants or transduction products which have the ability to produce the oxidase of the present invention, obtained in the above-described manner. For example, the oxidase of the present invention can be produced by using a transformant having the ability to produce the oxidase of the present invention and preferably belonging to the genus *Escherichia*. In culturing the above-described microorganism, it may be cultured by a solid culture method, but it is more desirable to carry out the culturing by employing a liquid culture method. In addition, the medium to be used in the culturing of the above-described microorganism is prepared, for example, by adding one or more inorganic salts of potassium dihydrogenphosphate, dipotassium hydrogenphosphate, magnesium sulfate, ferric chloride, ferric sulfate, manganese sulfate and the like to one or more nitrogen sources of yeast extract, peptone, meat extract, corn steep liquor, soybean or wheat cake extract and the like, and optionally adding sugar materials, vitamins and the like, if necessary. In this connection, it is proper that initial pH of the medium is adjusted to a value from 6 to 9. Also, it is desirable to carry out the culturing at a temperature of from 20 to 42° C., preferably at about 25° C., for a period of from 10 to 40 hours, by aeration agitation submerged culture, shaking culture, standing culture or the like. After completion of the culturing, a usual enzyme collection means can be used for collecting the oxidase of the present invention from the culture mixture. Cells are separated from the culture medium, for example, by operation such as filtration or centrifugation, and then washed. It is desirable to collect the oxidase of the present invention from such cells. In this case, the cells can be used as such, but it is desirable to collect the oxidase of the present invention from the cells by a method in which the cells are disrupted using various disruption means such as ultrasonic disintegrator, French press and Dynomill, a method in which cell walls are lysed using a cell wall lytic enzyme such as lysozyme, or a method in which the enzyme is extracted from the cells using a surfactant such as Triton X-100.

For the purpose of isolating the oxidase of the present invention from the crude enzyme liquid obtained in this manner, a method generally used in the enzyme purification can be used. It is desirable to carry out this by optionally combining, for example, ammonium sulfate salting out, organic solvent precipitation, ion exchange chromatography, gel filtration chromatography, adsorption chromatography and electrophoresis. In this manner, the oxidase of the present invention can be isolated at a level of purification until it shows almost a single band by SDS-PAGE. In addition, enzyme preparations having different purification degree can also be prepared in response to the uses, by optionally combining the above-described purification methods.

Regarding the method for measuring enzyme activity of the oxidase of the present invention, a method in which the amount of hydrogen peroxide formed by the enzyme reaction is measured and a method in which the amount of oxygen consumed by the enzyme reaction can be exemplified as the main measuring methods. In the following, unless otherwise noted, cholesterol is used as the substrate in the activity measurement of the enzyme of the present invention. In this connection, regarding the enzyme titer, the amount of enzyme which forms 1 μmol of hydrogen peroxide within 1 minute when measured using cholesterol as the substrate was defined as 1 U.

A. Preparation of Reagents (1) Reagent 1: Cholesterol Solution

Firstly, 500 mg of cholesterol (manufactured by Wako Pure Chemical Industries) is added to 5.0 ml of Triton X-100 and dissolved therein by stirring on a heater. Next 90 ml of ion exchange water is added thereto, the solution is boiled and then cooled on ice, 4.0 g of sodium cholate (manufactured by Nacalai Tesque) is added thereto and dissolved therein, and then the total volume is adjusted to 100 ml.

(2) Reagent 2; 6.0% Phenol Solution

In ion exchange water, 6.0 g of phenol is dissolved, and the total volume is adjusted to 100 ml.

(3) Reagent 3: 0.15% Peroxidase Solution

In 100 ml of 0.1 M potassium phosphate buffer (pH 7.0), 150 mg of peroxidase is dissolved (4) Reagent 4: 4-aminoantipyrine Solution In ion exchange water, 1.76 g of 4-aminoantipyrine (manufactured by Wako Pure Chemical Industries) is dissolved, and the total volume is adjusted to 100 ml.

B. Measuring Method

After mixing 4.0 ml of the reagent 1 with 51 ml of 0.1 M potassium phosphate buffer (pH 7.0), 2.0 ml of the reagent 2, 2.0 ml of the reagent 3 and 1.0 ml of the reagent 4 are added thereto in this order, followed by mixing. This is dispensed at 3.0 ml into test tubes and preserved under ice-cooling. At the time of the measurement, 3.0 ml thereof is incubated at 37° C. for 5 minutes, 50 μl of each enzyme liquid is added thereto, followed by mixing, and then the absorbance at 500 nm is measured by a spectrophotometer (U-3010, manufactured by Hitachi). The measured value (ΔODtest) is a change in absorbance at 500 nm per minute from after 2 minutes to after 4 minutes. In this connection, the control liquid (ΔODblank) was prepared in the same manner as described in the above, except that 50 μl of 20 mM potassium phosphate Buffer (pH 7.0) containing 0.2% bovine serum albumin was added instead of the enzyme liquid. The value calculated in accordance with the following calculating formula was used as the enzyme activity value (U/ml).

$$U/ml = \frac{\Delta OD/\min(\Delta ODtest - \Delta ODblank) \times 3.05 \text{ (ml)} \times \text{dilution ratio}}{13.78 \times 1/2 \times 1.0 \times 0.05 \text{ (ml)}}$$

13.78: millimole molar absorption coefficient (cm$^2$/micromole) under the above-described measuring conditions 1/2: a factor based on the fact that the Quinoneimine pigment formed from 2 molecules of $H_2O_2$ formed by the enzyme reaction is 1 molecule 1.0: optical path length (cm)

By using the cholesterol oxidase gene obtained by the present invention, a cholesterol oxidase which shows high activity at a low substrate (cholesterol) concentration, acts at broad pH values and is excellent in heat stability can be provided at a low cost. Since stability of the cholesterol oxidase to surfactants is improved, this is particularly suited for the measurement of cholesterol in body fluids and food. Also, since it is strongly activated under organic solvent overlay conditions, it has a characteristic in that enzymatic conversion of cholesterols can be efficiently carried out. In addition to these advantages, this enzyme can also be used as an insecticide through its oral ingestion, and also as a detergent for clothes and the like stained with cholesterols.

The present invention is described below in detail based on Examples; however, the present invention is not limited thereto.

EXAMPLE 1

(A) Preparation of Recombinant Plasmid

A recombinant plasmid DNA containing an oxidase gene having a different property (a gene encoding the amino acid sequence represented by SEQ ID NO:1) and, for the purpose of increasing expressed amount of this gene in *Escherichia coli*, another recombinant plasmid DNA containing an oxidase gene in which the nucleotide sequence of a region encoding the amino terminus of this gene was modified to fit to the codon usage of *E. coli* were respectively prepared. In preparing the oxidase of the present invention which is described below, both of the recombinant plasmid DNA can be used, but it is effective to use the recombinant plasmid DNA containing modified oxidase gene for the purpose of producing the oxidase of the present invention in a large amount.

(1) Preparation of Recombinant Plasmid pCox4 DNA

*E. coli* DH5α (pCox4) containing the above-described oxidase gene (a gene encoding the amino acid sequence represented by SEQ ID NO:1) was prepared according to the examples in JP-A-2002-65271 and was inoculated into 20 ml of LB medium (1% bacto-tryptone, 0.5% yeast extract and 0.25% NaCl) and cultured at 37° C. for 20 hours on a shaker to obtain a culture broth. This culture broth was centrifuged at 7,000 rpm for 5 minutes to recover the cells. The recombinant plasmid pCox4 DNA was extracted and purified from the cells using QIAGEN tip-100 (manufactured by Qiagen) to thereby obtain 100 μg of the recombinant plasmid pCox4 DNA.

(2) Preparation of Recombinant Plasmid pNCOP DNA in which Amino Terminus Side Nucleotide Sequence was Modified Oligonucleotides having the nucleotide sequences described in SEQ ID NOs:7 to 14 as partial sequences of SEQ ID NO:6 were obtained through the synthesis service on consignment of Sigma Genosis. Each of the SEQ ID NOs:7 to 14 was phosphorylated using T4 Polynucleotide kinase (manufactured by Takara Shuzo). On the other hand, a gene fragment encoding C terminal side was prepared by carrying out PCR using pCox4 DNA having SEQ ID NO:1 as the template, SEQ ID NOs:15 and 16 as the primers and using Ex Taq polymerase (manufactured by Takara Shuzo). Further, this fragment was treated with AdeI (manufactured by Daiichi Pure Chemicals) and NspI (manufactured by Daiichi Pure Chemicals). In addition, pKF19k DNA was treated with NdeI and then subjected to dephosphorylation by BAP treatment (a reagent manufactured by Takara Shuzo was used). Among the thus obtained phosphorylated oligonucleotides, 8 phosphorylated oligonucleotides were mixed with the pCox4 DNA-derived gene fragment and pKF19k fragment in appropriate amounts and ligated making use of Ligation Kit ver. 2 (manufactured by Takara Shuzo), and the obtained plasmid was named pNCOP. Subsequently, 100 μg of pNCOP DNA was prepared by the method described in (1).

(B) Preparation of the Oxidase of the Present Invention and Transformant having the Ability to Produce the Oxidase of the Present Invention (1) Modification Operation (Introduction of Mutation)

PCR was carried out using the above-described recombinant plasmid pNCOP DNA as the template, and SEQ ID NOs:17 and 25 as the primers. In this case, a mutation was introduced by inducing an amplification mistake through the addition of 10% DMSO. A DNA fragment obtained in this manner was treated with a restriction enzyme NdeI and then mixed with a fragment prepared by treating the plasmid pKF19k also with NdeI and carrying out dephosphorylation by BAP treatment (a reagent manufactured by Takara Shuzo was used), the mixture was ligated making use of Ligation Kit ver, 2 (manufactured by Takara Shuzo), and the *E. coli* JM109 (manufactured by TOYOBO) was transformed using the ligated product in accordance with the method of D. M. Morrison (*Methods in Enzymology,* 68, 326-331 (1979)) to thereby obtain about 2,500 transformants carrying the modified plasmids.

(2) Selection of Strain which Produces the Oxidase of the Present Invention

Firstly, all of the transformants obtained in the above were inoculated into 96-well plates in which each well contained 100 μl of sterilized LB medium containing 1 mM of IPTG and 50 μg/ml of kanamycin. JM109 carrying pNCOP was inoculated into 1 well of each plate and used as the negative control. The culturing was carried out at 25° C. for 24 hours. The resulting plates containing the thus obtained culture liquids were put into a freezer of −80° C. and kept for 1 hour for cell lysis. Thereafter, each of them was mixed on the plate with 100 mM MES-NaOH buffer (pH 7.0) containing 0.2% bovine serum albumin supplemented with 100 μl of 10% Emalgen 913, and the mixture was allowed to stand at 37° C. for 5 hours. Thereafter, 50 μl of each treated liquid was taken out and mixed with 50 μl of a reaction reagent of the following composition to carry out the reaction, and those in which the coloring was increased in comparison with the negative control were selected.

Cholesterol Solution, 15 m:

To 5.0 ml of Triton X-100, 500 mg of cholesterol (manufactured by Wako Pure Chemical Industries) is added, and dissolved therein by stirring on a heater. After 90 ml of ion exchange water is added thereto, the solution is boiled and then cooled on ice, 4.04 g of sodium cholate (manufactured by Nacalai Tesque) is added thereto and dissolved therein, and then the total volume is adjusted to 100 ml;
0.1 M Potassium phosphate buffer, pH 7.0, 17.5 ml;
1.76% 4-Aminoantipyrine solution, 3.5 ml;
6.0% Phenol solution, 7 ml;
0.15% Peroxidase solution, 7 ml:

In 100 ml of 0.1 M potassium phosphate buffer (pH 7.0), 150 mg of peroxidase is dissolved.

Each of the color-developed 10 strains selected herein was liquid-cultured in 2 ml of LB medium (50 μg of kanamycin was added), and the modified cholesterol oxidase encoded by the plasmid was produced. After the culturing, the thus obtained culture broth was disrupted by a sonicator and centrifuged at 8,000 rpm for 5 minutes, and 0.5 ml of the thus obtained crude enzyme extract was mixed with 0.5 ml of 100 mM MES-NaOH buffer (pH 7.0) containing 0.2% bovine serum albumin supplemented with 10% Emalgen 913, and the mixture was allowed to react at 37° C. overnight. By measuring activities of this reaction liquid and a 2-fold dilution of untreated crude enzyme extract, residual ratio of activity (activity of reaction liquid/activity of untreated crude enzyme extract) was calculated. The oxidase having a different property before the modification was cultured, extracted and heat-treated in the same manner and its activity was measured, and comparison of the residual ratio of activities was carried out to thereby obtain a modified cholesterol oxidase whose residual ratio of activity was improved from 40% to 80% A and 3 *E. coli* strains which produce the same. A plasmid pNCP1 which encodes 1 species (R1) of gene among them has been deposited on May 27, 2005 in International Patent Organism Depositary, National Institute of Advanced Industrial Science and Technology, as FERM BP-10343.

(3) Identification of Region where the Mutation Occurred

The plasmid carrying the modified cholesterol oxidase gene was recovered, the nucleotide sequence was determined using CEQ2000XL DNA analyzing system (manufactured by Beckman Coulter), and identification of the modified amino acid residues was carried out based on this.

As a result, it was found that in the case of the oxidase of the present invention (R1), as shown in SEQ ID NO:2, aspartic acid at position 175 in the amino acid sequence represented by SEQ ID NO:1 was substituted with asparagine. This corresponds to position 133 in SEQ ID NO:5. In the same manner, in the case of another oxidase of the present invention (R7), it was found that proline at position 173 in the amino acid sequence represented by SEQ ID NO:1 was substituted with leucine, and aspartic acid at position 220 was substituted with glutamic acid. In addition, these are mutation of regions which correspond to position 131 and position 178 in SEQ ID NO:5.

(4) Separation and Combination of Mutation Points

An attempt was made to introduce these mutation points each independently. That is, PCR was carried out using pNCOP DNA, the sequences of SEQ ID NOs:17 and 18 (being designed in such a manner that aspartic acid at position 133 in SEQ ID NO:5 is substituted with asparagine) as the primers and KOD plus polymerase (manufactured by TOYOBO), amplification of the DNA fragment which corresponds to the full length of the plasmid was confirmed by agarose gel electrophoresis, the fragment was treated with a restriction enzyme DpnI (acts upon methylated DNA; manufactured by Daiichi Pure Chemicals) and then transformed into the *E. coli* JM109, and then the transformants were selected using LB agar medium supplemented with kanamycin. The grown colonies were cultured using a liquid medium containing kanamycin to recover the plasmids carrying the cholesterol oxidase gene, and their nucleotide sequences were determined to confirm that the intended mutation was introduced. Site-specifically mutated cholesterol oxidase genes were obtained also at position 131 (proline is substituted with leucine) and position 178 (aspartic acid is substituted with glutamic acid) of SEQ ID NO:5 by the same method using SEQ ID NOs:19 and 20 at position 131, and SEQ ID NOs:21 and 22 at position 178, instead. In addition, a double mutant cholesterol oxidase gene was obtained using a plasmid carrying the thus obtained site-specifically mutated cholesterol oxidase genes, as the template. In this case, since the mutation points at position 131 and at position 133 are close to each other, this was carried out using SEQ ID NOs:23 and 24. A plasmid cawing a triple mutant cholesterol oxidase gene was further obtained.

(5) Mutation Points and Surfactant Resistance

Each of the *E. coli* JM109 strains obtained in the above carrying plasmids containing mutation type cholesterol oxidase genes having different mutation points was cultured in 10 ml of LB-kanamycin medium supplemented with 1.0 mM IPTG at 30° C. for 24 hours, and the thus obtained culture medium was centrifuged at 8,000 rpm for 5 minutes to collect the cells which were then suspended in 1 ml of 20 mM potassium phosphate buffer (pH 7.0). Thereafter, the cells were disrupted by a sonicator and centrifuged at 10,000 rpm for 10 minutes to recover the supernatant. After 200 μl of each of these crude enzyme extracts was mixed with 200 μl of 100 mM MS-NaOH buffer (pH 7.0) containing 0.2% bovine serum albumin supplemented with 2% Emalgen 913, the mixture was allowed to stand at 30° C. for 7 days, and the residual ratio of enzyme activity was compared with that of a case of allowing to stand at 30° C. for 7 days without applying the surfactant treatment (Table 1).

TABLE 1

Mutation points of mutation type cholesterol oxidase and preservation stability in the coexistence of Emalgen 913

| Cholesterol oxidase | Mutation* | | | Residual ratio of activity (%) |
|---|---|---|---|---|
| | P131L | D133N | D178E | |
| CHO (WT) | | | | 26.2 |
| CHO (R1) | | mutated | | 78.8 |
| CHO (R7) | mutated | | mutated | 70.0 |
| P131L | mutated | | | 79.3 |
| D133N | | mutated | | 80.0 |
| D178E | | | mutated | 23.7 |
| P131LD133N | mutated | mutated | | 106.5 |
| P131LD178E | mutated | | mutated | 71.1 |
| D133ND178E | | mutated | mutated | 91.8 |
| P131LD133ND178E | mutated | mutated | mutated | 100.0 |

*Mutation P131L: Substitution of proline at position 131 with leucine
Mutation D133N: Substitution of aspartic acid at position 133 with asparagine
Mutation D178E: Substitution of aspartic acid at position 178 with glutamic acid In addition, preservation stability upon other surfactants (Emalgen 120, Emal 20C and Emal 20CM) was examined on the mutation type cholesterol oxidase in which stabilizing effect for Emalgen 913 was observed. This test was carried out under the same conditions of the above test by mixing 200 μl of the crude enzyme extract with 200 μl of 100 mM MES-NaOH buffer (pH 7.0) containing 0.2% bovine serum albumin supplemented with 2% of respective surfactant and allowing the mixture to stand at 30° C. for 3 days (Table 2).

TABLE 2

Preservation stability upon surfactants

| Cholesterol oxidase | Residual ratio of activity in the presence of various surfactants (%) | | | |
|---|---|---|---|---|
| | Emalgen 913 | Emalgen 120 | Emal 20C | Emal 20CM |
| CHO (WT) | 41.1 | 25.6 | 17.8 | 71.1 |
| P131L | 90.2 | 54.9 | 31.4 | 82.3 |
| D133N | 90.3 | 51.3 | 40.7 | 86.7 |

TABLE 2-continued

Preservation stability upon surfactants

| Cholesterol oxidase | Residual ratio of activity in the presence of various surfactants (%) | | | |
|---|---|---|---|---|
| | Emalgen 913 | Emalgen 120 | Emal 20C | Emal 20CM |
| P131LD133N | 100.0 | 51.1 | 28.9 | 82.2 |
| P131LD178E | 81.0 | 44.1 | 40.5 | 79.8 |

(C) Production of the Oxidase of the Present Invention and Physicochemical Properties Thereof The thus obtained transformant *E. coli* JM109 (pNCP1) which produces the oxidase (R1) of the present invention was inoculated into 10 liters of LB-kanamycin medium containing 1 mM IPTG and cultured using a jar fermentor at 30° C. for 24 hours under conditions of 1 l/min aeration and 600 rpm agitation. Ten liters of the thus obtained culture medium was centrifuged at 7,000 rpm for 10 minutes to collect the cells which were then suspended in 1 liter of 20 mM potassium phosphate buffer (pH 7.0). Thereafter, the cells were disrupted by a sonicator and centrifuged at 10,000 rpm for 10 minutes to recover the supernatant to be used as a crude enzyme liquid. This crude enzyme liquid was subjected to a heat treatment at 60° C. for 30 minutes, diluted 10 times with 20 mM potassium phosphate buffer (pH 7.0) and then centrifuged at 10,000 rpm for 10 minutes to recover the supernatant. This was concentrated to 500 ml by dialyzing it against 5 mM EDTA-containing 20 mM Tris-HCl buffer (pH 8.8) using an ultrafiltration membrane AIP-2013 (manufactured by Asahi Chemical Industry). Thereafter, the mixture was suspended in 200 mM of QAE-Sephadex A-50 which had been equilibrated with 5 mM EDTA-containing 20 mM Tris-HCl buffer (pH 8.8), and the filtrate and the washings obtained by washing the residue with 5 mM EDTA-containing 20 mM Tris-HCl buffer (pH 8.8) were recovered as the active fractions. Specific activity of the thus recovered oxidase (RI) of the present invention was 4.0 U/A280.

Physicochemical properties of the thus obtained oxidase (RI) of the present invention were as follows.

(1) Action

Its reaction with cholesterol as the substrate was confirmed by the above-described enzyme activity measuring method.

(2) Optimum pH

Using 100 mM acetate buffer (pH 5.5 to 6.0), 100 mM potassium phosphate buffer (pH 6.0 to 8.22), 100 mM Tris-HCl buffer (pH 7.58 to 9.5) and 100 mM NaHCO$_3$—NaOH buffer (pH 9.43 to 11.0) as the buffers, the enzyme reaction was carried out at respective pH values at a temperature of 37° C. to find the relative activities as shown in FIG. 1. It was found from FIG. 1 that optimum pH of the oxidase of the present invention is from 6.5 to 8.0.

(3) Optimum Reaction Temperature Range

Figure 2:
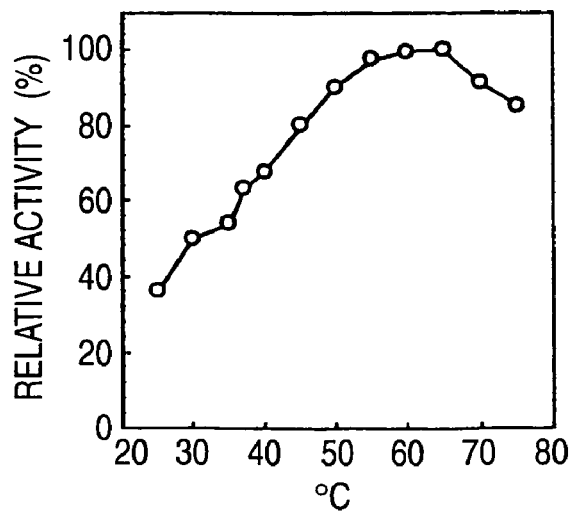
FIG. 2 is a graph showing an optimum reaction temperature range of the oxidase of the present invention.

Activity of this enzyme was measured at various temperatures using a reaction liquid consisting of the same composition of the reaction liquid used in the above-described activity measuring method, with the results shown in FIG. 2. As shown in FIG. 2, optimum reaction temperature range was from 55 to 65° C.

(4) Stable pH Range

Figure 3:
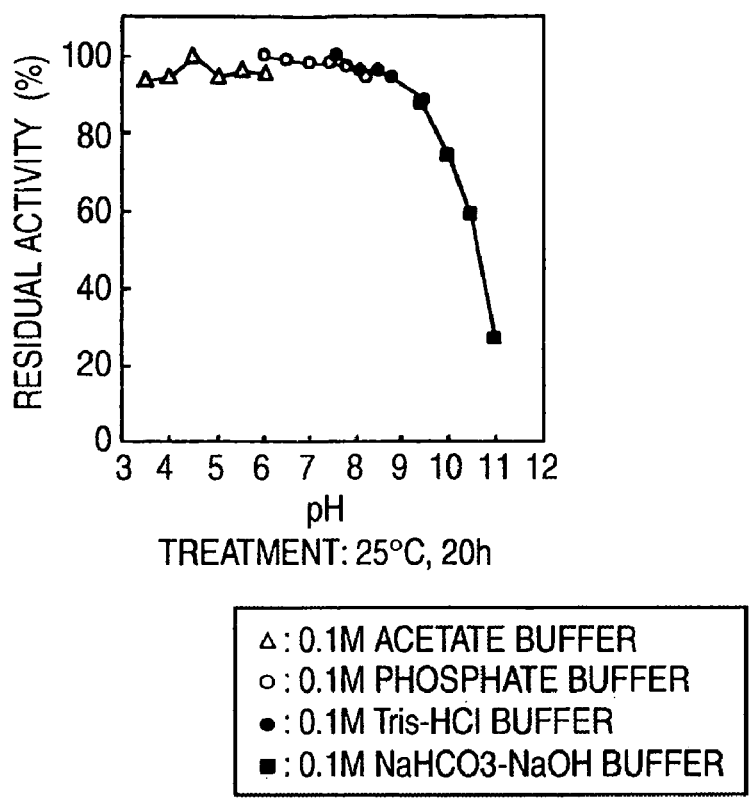
FIG. 3 is a graph showing a stable pH range of the oxidase of the present invention.

Using 100 mM acetate buffer (pH 3.5 to 6.0), 100 mM potassium phosphate buffer (pH 6.0 to 8.22), 100 mM Tris-HCl buffer (pH 7.58 to 9.5) and 100 mM NaHCO$_3$—NaOH buffer (pH 9.43 to 11.0) as the buffers, the oxidase of the present invention was treated at respective pH values at 25° C. for 20 hours and then the residual activities were measured, with the results shown in FIG. 3. As shown in FIG. 3, the stable pH range was from 3.5 to 8.5.

(5) Heat Stability

Figure 4:
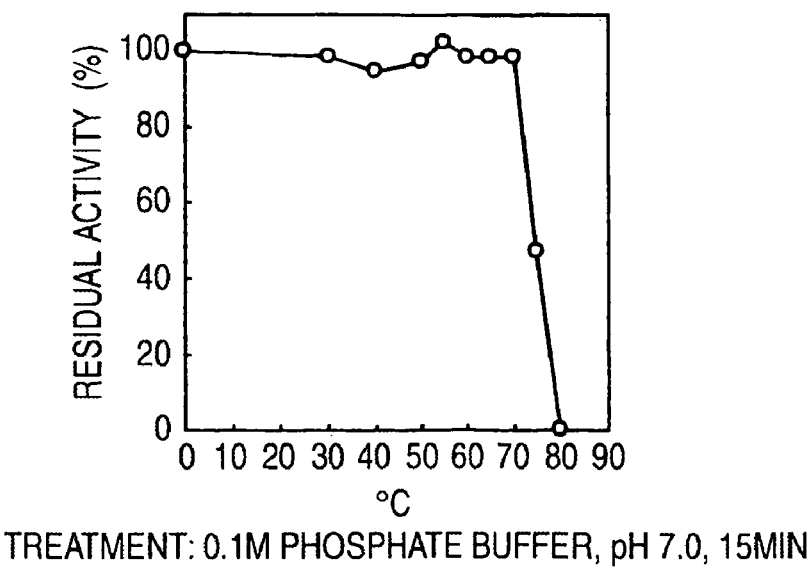
FIG. 4 is a graph showing heat stability of the oxidase of the present invention.

The enzyme was treated at respective temperatures for 15 minutes in 100 mM potassium phosphate buffer (pH 7.0) to measure its heat stability, with the results shown in FIG. 4. The oxidase of the present invention was stable at up to about 70° C.

(6) Molecular Weight

Molecular weight was obtained in the usual way by SDS-PAGE using Multigel 10/20 (manufactured by Daiichi Pure Chemicals). It was about 60,000.

(7) Surfactant Stability

Its stability to surfactants was compared with that of the original *Burkholderia cepacia* ST-200-derived cholesterol oxidase (CHO (WT)). Then, 100 mM NES-NaOH buffer (pH 7.0) containing 0.2% bovine serum albumin supplemented with 2% of each surfactant was mixed with the same amount of 2 U/ml cholesterol oxidase and stored at 37° C. for 24 hours (Table 3).

TABLE 3

Comparison of preservation stabilities of purified enzymes upon surfactants

|  | CHO (WT) | CHO (R1) |
|---|---|---|
| Emalgen 913 | 11.8 | 80.0 |
| Emalgen 120 | 10.5 | 65.0 |
| Emal 20C | 40.6 | 90.8 |
| Emal 20CM | 71.4 | 92.1 |

This application is based on Japanese patent application No. 2005-167779 filed on Jun. 8, 2005, the entire contents of which are incorporated hereinto by reference. While the invention has been described in detail and with reference to specific embodiments thereof, it will be apparent to one skill in the art that various changes and modifications can be made therein without departing from the spirit and scope thereof. All references cited herein are incorporated in their entirety.

What is claimed is:

1. An isolated protein having cholesterol oxidase activity, which is a protein comprising the amino acid sequence of SEQ ID NO: 5.

\* \* \* \* \*

SEQUENCE LISTING

```
<160> NUMBER OF SEQ ID NOS: 25

<210> SEQ ID NO 1
<211> LENGTH: 582
<212> TYPE: PRT
<213> ORGANISM: Burkholderia cepacia
<220> FEATURE:
<223> OTHER INFORMATION: ST-200

<400> SEQUENCE: 1

Met Ser Gln Asp Phe Arg Asp Glu Pro Ala Ser Arg Arg Ala Phe Leu
 1               5                  10                  15

Ala Asp Met Ala Lys Leu Ala Ala Ala Gly Val Val Thr Gly Trp Thr
             20                  25                  30

Pro Leu Tyr Gln Ile Ala Ala Asn Ala Arg Thr Ala Asp Ala Pro Pro
         35                  40                  45

Pro Gly Phe Pro Ala Asp Ile Pro Leu Tyr Lys Gln Ala Phe Gln Asn
     50                  55                  60

Trp Ser Gly Glu Ile Ala Val Gln Asp Val Trp Thr Ala Ala Pro Arg
 65                  70                  75                  80

Ser Ala Asp Asp Val Val Ala Ala Val Asn Trp Ala Arg Ala Asn Gly
                 85                  90                  95

Tyr Arg Ile Arg Pro Arg Gly Tyr Met His Asn Trp Ser Pro Leu Thr
            100                 105                 110

Leu Asp Pro Gly Ala Gly Ala Ala Asn Val Val Leu Leu Asp Thr Thr
        115                 120                 125

Lys Ser Leu Thr Ala Val Ser Val Asp Thr Ser Ala Arg Pro Ala Arg
    130                 135                 140

Val Thr Ala Gln Thr Gly Ile Ser Leu Glu Ser Leu Leu Ala Thr Leu
145                 150                 155                 160

Glu Gln Tyr Gly Leu Gly Val Ile Ala Ala Pro Ala Pro Gly Asp Ile
                165                 170                 175
```

-continued

```
Thr Leu Gly Gly Ala Leu Ala Ile Asp Ala His Gly Thr Ala Val Pro
            180                 185                 190

Ala Val Gly Glu Thr Leu Gln Pro Gly His Thr Tyr Gly Ser Leu Ser
        195                 200                 205

Asn Leu Val Val Ala Leu Thr Ala Val Val Tyr Asp Pro Ala Arg Gln
    210                 215                 220

Gln Tyr Val Leu Arg Arg Phe Glu Arg Ser Asp Pro Glu Ile Gly Ala
225                 230                 235                 240

Phe Leu Ala His Ile Gly Arg Ala Phe Val Val Glu Val Thr Leu Thr
                245                 250                 255

Ala Gly Pro Asn Gln Arg Leu Arg Cys Gln Ser Tyr Val Asp Ile Pro
            260                 265                 270

Ala Ser Glu Leu Phe Ala Pro Ala Gly Thr Ser Gly Arg Thr Ile Thr
        275                 280                 285

Ser Phe Leu Asp Arg Ala Gly Arg Val Glu Ala Ile Trp Phe Pro Phe
    290                 295                 300

Thr Ser Ser Pro Trp Leu Lys Val Trp Thr Pro Thr Pro Ser Lys Pro
305                 310                 315                 320

Phe Leu Ser Arg Ala Val Thr Gln Pro Tyr Asn Tyr Pro Phe Ser Asp
                325                 330                 335

Ser Ile Ser Gln Ser Ile Ser Asp Leu Val Lys Arg Ile Val Ile Gly
            340                 345                 350

Gly Glu Gly Ala Leu Thr Pro Leu Phe Gly Gln Thr Gln Leu Ala Ile
        355                 360                 365

Thr Ala Ala Gly Leu Ala Leu Thr Leu Ser Gly Asp Ile Trp Gly Trp
    370                 375                 380

Ser Arg Thr Val Leu Gln Tyr Ile Arg Pro Thr Thr Leu Arg Val Thr
385                 390                 395                 400

Ala Asn Gly Tyr Ala Val Leu Ala Arg Arg Ala Asp Val Gln Arg Val
                405                 410                 415

Ile Ser Glu Phe Val Gln Phe Tyr Gln Asn Arg Val Asp Thr Tyr Lys
            420                 425                 430

Ala Arg Gly Glu Tyr Pro Met Asn Gly Pro Val Glu Ile Arg Ile Thr
        435                 440                 445

Gly Leu Asp Lys Pro Ala Asp Ala Gly Ala Gly Ala Ala Val Pro Ser
    450                 455                 460

Leu Ser Ala Leu Lys Pro Arg Pro Asp Arg Pro Glu Trp Asp Val Ala
465                 470                 475                 480

Val Trp Phe Asp Ile Leu Thr Leu Pro Gly Thr Pro Ser Ala Asp Arg
                485                 490                 495

Phe Tyr Arg Glu Ile Glu Gln Trp Met Leu Ala Asn Tyr Thr Gly Ser
            500                 505                 510

Tyr Ala Thr Leu Arg Pro Glu Trp Ser Lys Gly Trp Gly Tyr Thr Asp
        515                 520                 525

Thr Ala Ala Trp Gln Asp Asp Thr Met Leu Thr Thr Ile Pro Asn
    530                 535                 540

Leu Gln Arg Glu Gly Gln Pro Ala Ser Ser Thr Trp Asp Thr Ala Arg
545                 550                 555                 560

Ala Thr Leu Glu Arg Tyr Asp Pro His Arg Ile Phe Arg Ser Pro Leu
                565                 570                 575

Leu Asp Arg Leu Met Pro
            580
```

<210> SEQ ID NO 2
<211> LENGTH: 582
<212> TYPE: PRT
<213> ORGANISM: Burkholderia cepacia
<220> FEATURE:
<223> OTHER INFORMATION: ST-200

<400> SEQUENCE: 2

```
Met Ser Gln Asp Phe Arg Asp Glu Pro Ala Ser Arg Arg Ala Phe Leu
 1               5                  10                  15

Ala Asp Met Ala Lys Leu Ala Ala Ala Gly Val Val Thr Gly Trp Thr
            20                  25                  30

Pro Leu Tyr Gln Ile Ala Ala Asn Ala Arg Thr Ala Asp Ala Pro Pro
        35                  40                  45

Pro Gly Phe Pro Ala Asp Ile Pro Leu Tyr Lys Gln Ala Phe Gln Asn
    50                  55                  60

Trp Ser Gly Glu Ile Ala Val Gln Asp Val Trp Thr Ala Ala Pro Arg
65                  70                  75                  80

Ser Ala Asp Asp Val Val Ala Ala Val Asn Trp Ala Arg Ala Asn Gly
                85                  90                  95

Tyr Arg Ile Arg Pro Arg Gly Tyr Met His Asn Trp Ser Pro Leu Thr
            100                 105                 110

Leu Asp Pro Gly Ala Gly Ala Ala Asn Val Val Leu Leu Asp Thr Thr
        115                 120                 125

Lys Ser Leu Thr Ala Val Ser Val Asp Thr Ser Ala Arg Pro Ala Arg
    130                 135                 140

Val Thr Ala Gln Thr Gly Ile Ser Leu Glu Ser Leu Leu Ala Thr Leu
145                 150                 155                 160

Glu Gln Tyr Gly Leu Gly Val Ile Ala Ala Pro Ala Pro Gly Asn Ile
                165                 170                 175

Thr Leu Gly Gly Ala Leu Ala Ile Asp Ala His Gly Thr Ala Val Pro
            180                 185                 190

Ala Val Gly Glu Thr Leu Gln Pro Gly His Thr Tyr Gly Ser Leu Ser
        195                 200                 205

Asn Leu Val Val Ala Leu Thr Ala Val Val Tyr Asp Pro Ala Arg Gln
    210                 215                 220

Gln Tyr Val Leu Arg Arg Phe Glu Arg Ser Asp Pro Glu Ile Gly Ala
225                 230                 235                 240

Phe Leu Ala His Ile Gly Arg Ala Phe Val Val Glu Val Thr Leu Thr
                245                 250                 255

Ala Gly Pro Asn Gln Arg Leu Arg Cys Gln Ser Tyr Val Asp Ile Pro
            260                 265                 270

Ala Ser Glu Leu Phe Ala Pro Ala Gly Thr Ser Gly Arg Thr Ile Thr
        275                 280                 285

Ser Phe Leu Asp Arg Ala Gly Arg Val Glu Ala Ile Trp Phe Pro Phe
    290                 295                 300

Thr Ser Ser Pro Trp Leu Lys Val Trp Thr Pro Thr Pro Ser Lys Pro
305                 310                 315                 320

Phe Leu Ser Arg Ala Val Thr Gln Pro Tyr Asn Tyr Pro Phe Ser Asp
                325                 330                 335

Ser Ile Ser Gln Ser Ile Ser Asp Leu Val Lys Arg Ile Val Ile Gly
            340                 345                 350

Gly Glu Gly Ala Leu Thr Pro Leu Phe Gly Gln Thr Gln Leu Ala Ile
        355                 360                 365

Thr Ala Ala Gly Leu Ala Leu Thr Leu Ser Gly Asp Ile Trp Gly Trp
```

```
                370             375             380
Ser Arg Thr Val Leu Gln Tyr Ile Arg Pro Thr Thr Leu Arg Val Thr
385                 390                 395                 400

Ala Asn Gly Tyr Ala Val Leu Ala Arg Arg Ala Asp Val Gln Arg Val
            405                 410                 415

Ile Ser Glu Phe Val Gln Phe Tyr Gln Asn Arg Val Asp Thr Tyr Lys
        420                 425                 430

Ala Arg Gly Glu Tyr Pro Met Asn Gly Pro Val Glu Ile Arg Ile Thr
            435                 440                 445

Gly Leu Asp Lys Pro Ala Asp Ala Gly Ala Gly Ala Ala Val Pro Ser
450                 455                 460

Leu Ser Ala Leu Lys Pro Arg Pro Asp Arg Pro Glu Trp Asp Val Ala
465                 470                 475                 480

Val Trp Phe Asp Ile Leu Thr Leu Pro Gly Thr Pro Ser Ala Asp Arg
                485                 490                 495

Phe Tyr Arg Glu Ile Glu Gln Trp Met Leu Ala Asn Tyr Thr Gly Ser
            500                 505                 510

Tyr Ala Thr Leu Arg Pro Glu Trp Ser Lys Gly Trp Gly Tyr Thr Asp
        515                 520                 525

Thr Ala Ala Trp Gln Asp Asp Thr Met Leu Thr Thr Ile Pro Asn
530                 535                 540

Leu Gln Arg Glu Gly Gln Pro Ala Ser Ser Thr Trp Asp Thr Ala Arg
545                 550                 555                 560

Ala Thr Leu Glu Arg Tyr Asp Pro His Arg Ile Phe Arg Ser Pro Leu
                565                 570                 575

Leu Asp Arg Leu Met Pro
            580

<210> SEQ ID NO 3
<211> LENGTH: 1749
<212> TYPE: DNA
<213> ORGANISM: Burkholderia cepacia
<220> FEATURE:
<223> OTHER INFORMATION: ST-200

<400> SEQUENCE: 3
atgagtcaag acttccgaga cgaaccagcg tcgcgccgcg ctttcctcgc cgacatggcg      60
aagctcgcgg ccgcaggcgt cgtcaccggc tggacgccgc tctaccagat tgcggccaat     120
gcgcgaaccg ccgacgcgcc gccgcccggc ttcccggccg acatcccgct ttacaagcag     180
gcgttccaga actggagcgg tgaaatcgcc gtgcaggacg tatggaccgc cgcgccgcgc     240
tcggccgacg atgtcgtcgc ggcggtcaac tgggcgcgcg cgaacggcta ccggatccgc     300
ccgcgcggct acatgcacaa ctggtcgccg ctcacgctgg atccgggcgc cggcgccgcg     360
aacgtggtgc tgctcgatac gacgaaatcg ctgacgccg tctcggtcga cacgtcggca      420
cgtccggcgc gcgtcaccgc ccaaacgggc atctcgctgg agtcgttgct cgcgacgctc     480
gaacagtatg gcctcggcgt gattgccgcg cctgcgccgg cgacatcac gctcggcggt      540 gcgctcgcga tcgatgcgca cggcactgcc gtgccggcgg tcggtgaaac cttgcaaccg     600
ggacacacct acggctcgct gagcaacctc gtggtcgcgc tcaccgcggt cgtgtacgat     660
ccggcccggc agcaatacgt gctgcgccgg ttcgaacgca gcgatcccga gatcggcgcg     720
ttcctcgcgc acatcgggcg ggcgttcgtc gtcgaagtca cgctgacggc aggccccaac     780
cagcgcctgc gctgccagag ctacgtcgac attccggcct ccgaactgtt tgcgccggcc     840
```

```
ggcacgtcgg gccgcacgat cacgtcgttt ctcgatcgcg cgggccgggt ggaagccatc     900
tggtttccgt ttacgtccag cccgtggctc aaggtctgga cgcccacgcc cagcaagccg     960
ttcctgtcgc gcgccgtcac gcagccgtac aactatccgt tctccgattc gatctcgcag    1020
tccatctcgg atctcgtcaa gcggatcgtg atcggcggcg aaggcgcatt gacgccgctg    1080
ttcggccaga cgcaattggc catcacggcc gccggtctcg cgctcacgct cagcggggat    1140
atctggggct ggtcgcgcac cgtgctgcag tacattcgac cgacgacgct cgcgtgacc     1200 gcgaacggct atgcggtact ggcgcggcgc gccgacgtgc agcgcgtgat cagcgagttc    1260
gtgcagttct atcagaaccg cgtcgacacg tacaaggcgc gcggcgagta tccgatgaac    1320
ggtcccgtcg agatccgcat caccggtctc gacaagccgg ccgatgccgg cgccggcgcg    1380
gccgtgccca gcctgtccgc actcaagccg cgccccgacc ggccggagtg ggacgtggcc    1440
gtgtggttcg atattctgac gttaccgggc acgccgtccg ccgatcgctt ctatcgcgag    1500
atcgagcaat ggatgctcgc gaactacacc ggttcgtatg cgacgctgcg ccccgaatgg    1560
tcgaagggtt ggggctatac cgatacggct gcctggcaag acgacacgat gctcaccacc    1620
acgattccga acctgcaacg tgaagggcag ccggcgtcga gcacgtggga tacggcgcgc    1680
gcgacgctcg aacgctacga cccgcaccgg atcttccgct cgccgctgct ggatcggttg    1740
atgccgtaa                                                            1749

<210> SEQ ID NO 4
<211> LENGTH: 1749
<212> TYPE: DNA
<213> ORGANISM: Burkholderia cepacia
<220> FEATURE:
<223> OTHER INFORMATION: ST-200

<400> SEQUENCE: 4
atgagtcaag acttccgaga cgaaccagcg tcgcgccgcg ctttcctcgc cgacatggcg      60
aagctcgcgg ccgcaggcgt cgtcaccggc tggacgccgc tctaccagat tgcggccaat     120
gcgcgaaccg ccgacgcgcc gccgcccggc ttcccggccg acatcccgct ttacaagcag     180
gcgttccaga actggagcgg tgaaatcgcc gtgcaggacg tatggaccgc cgcgccgcgc     240
tcggccgacg atgtcgtcgc ggcggtcaac tgggcgcgcg cgaacggcta ccggatccgc     300
ccgcgcggct acatgcacaa ctggtcgccg ctcacgctgg atccgggcgc cggcgccgcg     360
aacgtggtgc tgctcgatac gacgaaatcg ctgacggccg tctcggtcga cacgtcggca     420
cgtccggcgc gcgtcaccgc ccaaacgggc atctcgctgg agtcgttgct cgcgacgctc     480
gaacagtatg gcctcggcgt gattgccgcg cctgcgccgg caacatcac gctcggcggt      540 gcgctcgcga tcgatgcgca cggcactgcc gtgccggcg tcggtgaaac cttgcaaccg      600
ggacacacct acggctcgct gagcaacctc gtggtcgcgc tcaccgcggt cgtgtacgat     660
ccggcccggc agcaatacgt gctgcgccgg ttcaacgca gcgatcccga gatcggcgcg      720
ttcctcgcgc acatcgggcg ggcgttcgtc gtcgaagtca cgctgacggc aggccccaac     780
cagcgcctgc gctgccagag ctacgtcgac attccggcct ccgaactgtt tgcgccggcc     840
ggcacgtcgg gccgcacgat cacgtcgttt ctcgatcgcg cgggccgggt ggaagccatc     900
tggtttccgt ttacgtccag cccgtggctc aaggtctgga cgcccacgcc cagcaagccg     960
ttcctgtcgc gcgccgtcac gcagccgtac aactatccgt tctccgattc gatctcgcag    1020
tccatctcgg atctcgtcaa gcggatcgtg atcggcggcg aaggcgcatt gacgccgctg    1080
ttcggccaga cgcaattggc catcacggcc gccggtctcg cgctcacgct cagcggggat    1140
```

```
atctggggct ggtcgcgcac cgtgctgcag tacattcgac cgacgacgct gcgcgtgacc   1200
gcgaacggct atgcggtact ggcgcggcgc gccgacgtgc agcgcgtgat cagcgagttc   1260
gtgcagttct atcagaaccg cgtcgacacg tacaaggcgc gcggcgagta tccgatgaac   1320
ggtcccgtcg agatccgcat caccggtctc gacaagccgg ccgatgccgg cgccggcgcg   1380
gccgtgccca gcctgtccgc actcaagccg cgccccgacc ggccggagtg ggacgtggcc   1440
gtgtggttcg atattctgac gttaccgggc acgccgtccg ccgatcgctt ctatcgcgag   1500
atcgagcaat ggatgctcgc gaactacacc ggttcgtatg cgacgctgcg ccccgaatgg   1560
tcgaagggtt ggggctatac cgatacggct gcctggcaag acgacacgat gctcaccacc   1620
acgattccga acctgcaacg tgaagggcag ccggcgtcga gcacgtggga tacggcgcgc   1680
gcgacgctcg aacgctacga cccgcaccgg atcttccgct cgccgctgct ggatcggttg   1740
atgccgtaa                                                           1749
```

<210> SEQ ID NO 5
<211> LENGTH: 540
<212> TYPE: PRT
<213> ORGANISM: Burkholderia cepacia
<220> FEATURE:
<223> OTHER INFORMATION: ST-200

<400> SEQUENCE: 5

```
Met Ala Asp Ala Pro Pro Pro Gly Phe Pro Ala Asp Ile Pro Leu Tyr
  1               5                  10                  15

Lys Gln Ala Phe Gln Asn Trp Ser Gly Glu Ile Ala Val Gln Asp Val
             20                  25                  30

Trp Thr Ala Ala Pro Arg Ser Ala Asp Asp Val Val Ala Ala Val Asn
         35                  40                  45

Trp Ala Arg Ala Asn Gly Tyr Arg Ile Arg Pro Arg Gly Tyr Met His
     50                  55                  60

Asn Trp Ser Pro Leu Thr Leu Asp Pro Gly Ala Gly Ala Ala Asn Val
65                  70                  75                  80

Val Leu Leu Asp Thr Thr Lys Ser Leu Thr Ala Val Ser Val Asp Thr
                85                  90                  95

Ser Ala Arg Pro Ala Arg Val Thr Ala Gln Thr Gly Ile Ser Leu Glu
            100                 105                 110

Ser Leu Leu Ala Thr Leu Glu Gln Tyr Gly Leu Gly Val Ile Ala Ala
        115                 120                 125

Pro Ala Pro Gly Asn Ile Thr Leu Gly Gly Ala Leu Ala Ile Asp Ala
    130                 135                 140

His Gly Thr Ala Val Pro Ala Val Gly Glu Thr Leu Gln Pro Gly His
145                 150                 155                 160

Thr Tyr Gly Ser Leu Ser Asn Leu Val Val Ala Leu Thr Ala Val Val
                165                 170                 175

Tyr Asp Pro Ala Arg Gln Gln Tyr Val Leu Arg Arg Phe Glu Arg Ser
            180                 185                 190

Asp Pro Glu Ile Gly Ala Phe Leu Ala His Ile Gly Arg Ala Phe Val
        195                 200                 205

Val Glu Val Thr Leu Thr Ala Gly Pro Asn Gln Arg Leu Arg Cys Gln
    210                 215                 220

Ser Tyr Val Asp Ile Pro Ala Ser Glu Leu Phe Ala Pro Ala Gly Thr
225                 230                 235                 240

Ser Gly Arg Thr Ile Thr Ser Phe Leu Asp Arg Ala Gly Arg Val Glu
```

```
                   245                 250                 255
Ala Ile Trp Phe Pro Phe Thr Ser Ser Pro Trp Leu Lys Val Trp Thr
            260                 265                 270

Pro Thr Pro Ser Lys Pro Phe Leu Ser Arg Ala Val Thr Gln Pro Tyr
            275                 280                 285

Asn Tyr Pro Phe Ser Asp Ser Ile Ser Gln Ser Ile Ser Asp Leu Val
            290                 295                 300

Lys Arg Ile Val Ile Gly Gly Glu Gly Ala Leu Thr Pro Leu Phe Gly
305                 310                 315                 320

Gln Thr Gln Leu Ala Ile Thr Ala Ala Gly Leu Ala Leu Thr Leu Ser
            325                 330                 335

Gly Asp Ile Trp Gly Trp Ser Arg Thr Val Leu Gln Tyr Ile Arg Pro
            340                 345                 350

Thr Thr Leu Arg Val Thr Ala Asn Gly Tyr Ala Val Leu Ala Arg Arg
            355                 360                 365

Ala Asp Val Gln Arg Val Ile Ser Glu Phe Val Gln Phe Tyr Gln Asn
            370                 375                 380

Arg Val Asp Thr Tyr Lys Ala Arg Gly Glu Tyr Pro Met Asn Gly Pro
385                 390                 395                 400

Val Glu Ile Arg Ile Thr Gly Leu Asp Lys Pro Ala Asp Ala Gly Ala
            405                 410                 415

Gly Ala Ala Val Pro Ser Leu Ser Ala Leu Lys Pro Arg Pro Asp Arg
            420                 425                 430

Pro Glu Trp Asp Val Ala Val Trp Phe Asp Ile Leu Thr Leu Pro Gly
            435                 440                 445

Thr Pro Ser Ala Asp Arg Phe Tyr Arg Glu Ile Glu Gln Trp Met Leu
            450                 455                 460

Ala Asn Tyr Thr Gly Ser Tyr Ala Thr Leu Arg Pro Glu Trp Ser Lys
465                 470                 475                 480

Gly Trp Gly Tyr Thr Asp Thr Ala Ala Trp Gln Asp Asp Thr Met Leu
            485                 490                 495

Thr Thr Thr Ile Pro Asn Leu Gln Arg Glu Gly Gln Pro Ala Ser Ser
            500                 505                 510

Thr Trp Asp Thr Ala Arg Ala Thr Leu Glu Arg Tyr Asp Pro His Arg
            515                 520                 525

Ile Phe Arg Ser Pro Leu Leu Asp Arg Leu Met Pro
            530                 535                 540

<210> SEQ ID NO 6
<211> LENGTH: 1623
<212> TYPE: DNA
<213> ORGANISM: Burkholderia cepacia
<220> FEATURE:
<223> OTHER INFORMATION: ST-200

<400> SEQUENCE: 6
atggcagatg cgccaccgcc aggttttccg gcagatattc gctttataa acaagcgttt      60 cagaattgga gcggtgaaat tgcagttcag gatgtttgga ctgcagcgcc gcgttctgca    120
gatgatgttg ttgcggcggt taattgggcg cgtgcgaatg ttatcgtat cgtccacgt     180 ggttacatgc acaactggtc gccgctcacg ctggatccgg cgccggcgc cgcgaacgtg    240 gtgctgctcg atacgacgaa atcgctgacg gccgtctcgg tcgacacgtc ggcacgtccg    300
gcgcgcgtca ccgcccaaac gggcatctcg ctggagtcgt tgctcgcgac gctcgaacag    360
tatggcctcg gcgtgattgc cgcgcctgcg ccgggcaaca tcacgctcgg cggtgcgctc    420
```

```
gcgatcgatg cgcacggcac tgccgtgccg gcggtcggtg aaaccttgca accgggacac    480
acctacggct cgctgagcaa cctcgtggtc gcgctcaccg cggtcgtgta cgatccggcc    540
cggcagcaat acgtgctgcg ccggttcgaa cgcagcgatc ccgagatcgg cgcgttcctc    600
gcgcacatcg gcgggcgtt cgtcgtcgaa gtcacgctga cggcaggccc caaccagcgc     660
ctgcgctgcc agagctacgt cgacattccg gcctccgaac tgtttgcgcc ggccggcacg    720
tcgggccgca cgatcacgtc gtttctcgat cgcgcgggcc gggtggaagc catctggttt    780
ccgtttacgt ccagcccgtg gctcaaggtc tggacgccca cgcccagcaa gccgttcctg    840
tcgcgcgccg tcacgcagcc gtacaactat ccgttctccg attcgatctc gcagtccatc    900
tcggatctcg tcaagcggat cgtgatcggc ggcgaaggcg cattgacgcc gctgttcggc    960
cagacgcaat tggccatcac ggccgccggt ctcgcgctca cgctcagcgg ggatatctgg   1020
ggctggtcgc gcaccgtgct gcagtacatt cgaccgacga cgctgcgcgt gaccgcgaac   1080
ggctatgcgg tactggcgcg gcgcgccgac gtgcagcgcg tgatcagcga gttcgtgcag   1140
ttctatcaga accgcgtcga cacgtacaag gcgcgcggcg agtatccgat gaacggtccc   1200
gtcgagatcc gcatcaccgg tctcgacaag ccggccgatg ccggcgccgg cgcggccgtg   1260
cccagcctgt ccgcactcaa gccgcgcccc gaccggccgg agtgggacgt ggccgtgtgg   1320
ttcgatattc tgacgttacc gggcacgccg tccgccgatc gcttctatcg cgagatcgag   1380
caatggatgc tcgcgaacta caccggttcg tatgcgacgc tgcgcccga atggtcgaag    1440 ggttggggct ataccgatac ggctgcctgg caagacgaca cgatgctcac caccacgatt   1500
ccgaacctgc aacgtgaagg cagccggcg tcgagcacgt gggatacggc gcgcgcgacg    1560
ctcgaacgct acgacccgca ccggatcttc cgctcgccgc tgctggatcg gttgatgccg   1620
taa                                                                 1623
```

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthesized
      oligonucleotide

<400> SEQUENCE: 7
tatggcagat gcgccaccgc caggttttcc ggcagatatt cc                       42

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthesized
      oligonucleotide

<400> SEQUENCE: 8
taaccacgtg gacgaatacg ataaccattc gcacgcgcc                           39

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Synthesized
      oligonucleotide

<400> SEQUENCE: 9
gctttataaa caagcgtttc agaattggag cggtgaaatt gcagttca                48

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Synthesized
      oligonucleotide

<400> SEQUENCE: 10
caattaaccg ccgcaacaac atcatctgca gaacgcggcg ctgcagtc                48

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthesized
      oligonucleotide

<400> SEQUENCE: 11
ggatgtttgg actgcagcgc cgcgttctgc agatgatgtt gttgcggc                48

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Synthesized
      oligonucleotide

<400> SEQUENCE: 12
caaacatcct gaactgcaat ttcaccgctc caattctgaa acgcttgt                48

<210> SEQ ID NO 13
<211> LENGTH: 52
<212> TYPE: DNA
<213> ORGANISM: Artificial Sequence
<220> FEATURE:
<223> OTHER INFORMATION: Description of Artificial Sequence: Synthesized
      oligonucleotide

<400> SEQUENCE: 13
ggttaattgg gcgcgtgcga atggttatcg tattcgtcca cgtggttaca tg          52

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthesized
      oligonucleotide

<400> SEQUENCE: 14
ttataaagcg gaatatctgc cggaaaacct ggcggtggcg catctgcca             49

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthesized
      Primer

<400> SEQUENCE: 15
cgtggttaca tgcacaactg gtcgccgctc                                      30

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthesized
      Primer

<400> SEQUENCE: 16
ggaattccat atgttacggc atcaaccgat ccag                                 34

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthesized
      Primer

<400> SEQUENCE: 17
cctgcgccgg gcaacatcac gctgggc                                         27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthesized
      Primer

<400> SEQUENCE: 18
ggcgagcgtg atgttgcccg gcgcagg                                         27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthesized
      Primer

<400> SEQUENCE: 19
gccgcgcctg cgctgggcga catcacg                                         27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthesized
      Primer

<400> SEQUENCE: 20
cgtgatgtcg cccagcgcag gcgcggc                                         27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthesized
      Primer

<400> SEQUENCE: 21
gcggtcgtgt acgagccggc ccggcag                                         27

```
<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthesized
      Primer

<400> SEQUENCE: 22
ctgccgggcc ggctcgtaca cgaccgc                                              27

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthesized
      Primer

<400> SEQUENCE: 23
gccgcgcctg cgctgggcaa catcacgctc ggc                                       33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthesized
      Primer

<400> SEQUENCE: 24
gccgagcgtg atgttgccca gcgcaggcgc ggc                                       33

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthesized
      Primer

<400> SEQUENCE: 25
aggaggtttc atatggcaga tgcgcc                                               26
```